United States Patent [19]

Lyons

[11] 4,021,369

[45] May 3, 1977

[54] ION-EXCHANGED TRANSITION METAL CATALYSTS FOR THE DIRECT OXIDATION OF OLEFINS TO EPOXYALCOHOLS

[75] Inventor: James E. Lyons, Wallingford, Pa.

[73] Assignee: Sun Ventures, Inc., Radnor, Pa.

[22] Filed: Feb. 5, 1975

[21] Appl. No.: 547,424

Related U.S. Application Data

[62] Division of Ser. No. 375,195, June 29, 1973, abandoned.

[52] U.S. Cl. .......................... 252/428; 252/455 Z; 260/348.5 V
[51] Int. Cl.² ................... B01J 31/02; B01J 29/06; C07D 301/24
[58] Field of Search ...................... 252/428, 455 Z; 260/348.5 V

[56] References Cited

UNITED STATES PATENTS

| 2,971,904 | 2/1961 | Gladrow et al. | 252/455 Z |
| 3,253,887 | 5/1966 | Mattox et al. | 252/455 Z |
| 3,345,284 | 10/1967 | Ogden | 252/428 X |
| 3,454,363 | 7/1969 | Rieve | 423/461 |
| 3,542,509 | 11/1970 | Furtig et al. | 252/455 Z |

Primary Examiner—Carl F. Dees
Attorney, Agent, or Firm—J. Edward Hess; Donald R. Johnson; Stanford M. Back

[57] ABSTRACT

Acylic or cyclic epoxyalcohols can be prepared by direct oxidation of an olefin when there is employed a ion-exchanged bimetallic catalyst, wherein one metal is from Groups IB or VIII, and the other from Group V or VI.

1 Claim, No Drawings

ION-EXCHANGED TRANSITION METAL CATALYSTS FOR THE DIRECT OXIDATION OF OLEFINS TO EPOXYALCOHOLS

This is a division of application Ser. No. 375,195, filed June 29, 1973 now abandoned.

BACKGROUND OF THE INVENTION

This invention relates to a novel method for the preparation of epoxyalcohols. More particularly, this invention is directed to the oxidation of acyclic or cyclic olefins to form the corresponding epoxyalconols in the presence of an ion-exchanged bimetallic catalyst in which the metals are valence-bonded to an anionic support. Epoxyalcohols are useful as intermediates in the preparation of glycerine and related compounds. Thus, for example glycidol (from propylene) would give glycerine when hydrolyzed. Similarly, 1,2-epoxy-3-hydroxy-2,3-dimethylbutene can be hydrolyzed to form the corresponding substituted glycerine which could have utility as a humectant and as a trifunctional monomer in the preparation of polymers.

Cyclic olefins, such as cyclohexene, when converted to the corresponding 1,2-epoxy-3-hydroxy-cyclohexane, may be dehydrogenated to form catechol. Substituted cyclohexenes yield the corresponding epoxyalcohols which can be dehydrogenated to yield substituted dihydroxybenzenes.

This invention also relates to certain novel metal-exchanged catalysts per se which are useful in the aforedescribed epoxidation process.

Van Sickle et al, J. Catal. 19, 209 (1970), disclosed the use of cobalt-exchanged zeolites as catalysts for the unselective oxidation of olefins to form a mixture of ketones and unsaturated alcohols, along with a minor amount of epoxides in some cases. U.S. Pat. No. 3,641,066 (1972) teaches a similar process wherein molybdenum, tungsten, or vanadium-exchanged zeolite catalysts are employed in the formation of olefin epoxides. In neither case, however, the epoxy-alcohols obtained as reaction products. Finally, belgian Patent No. 640,204 teaches the preparation of epoxyalcohols from olefins using as a catalyst system a compound derived from metals of Group IVA, VA, or VIA of the Periodic System, plus an alkylnydroperoxide and a radical initiator.

SUMMARY OF THE INVENTION

It has now been found, in accordance with the present invention, that acyclic and cyclic olefins may be oxidized to form the corresponding epoxyalcohols when there is employed as the catalyst a solid anionic material to which there is valence-bonded two different metals, one from Group IB or VIII, and the other from Group V or VI, of the Periodic Table.

The bi-metallic systems have the advantage that (1, they can be used without the necessity of added alkylhydroperoxides or initiators, (2) the solid catalyst is easily recoverable by filtration and may be reused many times without loss of activity, and (3) high yields of epoxyalcohols are possible using these catalyst systems.

DESCRIPTION OF THE INVENTION

The olefin starting materials may be any linear or branched, cyclic or acylic monoolefin or diolefin of the general formula

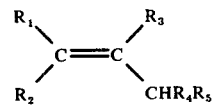

in which each of $R_1$, $R_2$, $R_3$, $R_4$, and $R_5$ may be the same or different, and are selected from the group consisting of hydrogen, lower alkyl, aryl, aralkyl, allyl, and alkenyl, and wherein $R_1$ and $R_3$ taken together may form a $C_5$ to $C_{10}$ cyclic hydrocarbon moiety. Included amongst these compounds are such olefins as tetramethylethylene, 2-ethylbutene-1, pentene-1, pentene-2, hexene-2, 2-methylpentene-2, 4-ethylpentene-2, cyclopentene, cyclohexene, methyl-substituted cyclohexenes, and fused ring alicyclic hydrocarbons such as dihydronaphthalene or indene. Preferred amongst these materials are cyclohexene and 1-methylcyclohexene.

When the aforedescribed olefins are oxidized in accordance with the process of the invention, there are obtained 1,2-epoxy-3-hydroxy derivatives of the general formula

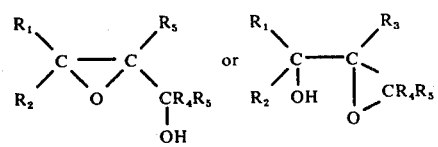

wherein each of $R_1$, $R_2$, $R_3$, $R_4$, and $R_5$ is as described above.

The catalyst used to effect the conversion of the aforesaid olefins to the epoxyalcohol is an ion-exchanged bimetallic solid catalyst, i.e., one in which the positive ions which are valence-bonded to an anionic support, as distinguished from conventional supported catalysts where the metal is deposited on, coated on, precpitated with a neutral, non-ionic support such as pumice, carbon kiesulguhr, alumina, or the like.

By "bimetallic" is meant that the anionic support must contain two different transition metal cations, each ionically bound to the support. One metal must be from Group V or VI of the Periodic Table, and preferably is vanadium, while the other metal must be from Group IB or VIII, and preferably should be cobalt, copper, iron, rhodium, ruthenium, osmium, or iridium.

The anionic support to which the metals are valence-bonded, may be any material having anionic sites which may be conveniently substituted with metals by conventional exchange methods. Thus, for example, suitable supports include faujasites, i.e., X- and Y-zeolites; mordenites, and ion-exchange resins, such as Amberlyst 15, and the like.

The catalysts of this invention may be prepared by any known exchange method wherein cations are substituted on anionic sites on the above-described supports. Thus, for example, using an X-type alumino-silicate zeolite as the support, a catalyst may be prepared by ion exchanging alkali metal-containing zeolites with transition metal ions which replace the alkali ions. Transition metal ion exchange can readily be effected, for example, with solutions of the salts of the metals such as their halides, sulfates, nitrates, and the like. Thus, for instance, a cobalt and vanadium exchanged X-zeolite catalyst may readily be prepared by first exchanging a sodium-exchanged X-zeolite with cobaltous chloride or nitrate until substantially all of the sodium is replaced by cobalt. The cobalt is then partially back-exchanged with a solution of a soluble vanadium salt such as vanadium oxysulfate to provide a zeolite containing both cobalt and vanadium ions in varying amounts depending on the quantity of vandium used in the exchange.

The weight ratio of the two exchanged metals to each other on the anionic support is critical in the sense that for any given pair of metals there will be an optimum ratio which provides the fastest rate and an optimum ratio which provides for greatest selectivity of epoxyols. These parameters can only be determined empirically by running a series of oxidations as described herein, noting the rates and selectivities for each run, and then selecting the two figures which provide the optimum results, preferably by optimizing selectivity and then choosing the desired rate.

Thus, for example, a cobalt- and vanadium-exchanged X-zeolite catalyst was employed in the oxidation of cyclohexene to the corresponding epoxyol, with the following result:

| Catalyst (0-15 Exchanges)* | % Co | % V | % Yield After 6 Hrs. | Selectivity to Epoxy-ol |
|---|---|---|---|---|
| Co-V-0 | 15.5 | 0.0 | 30% | 0% |
| Co-V-1 | 14.8 | 1.1 | 36% | 39% |
| Co-V-5 | 9.4 | 3.9 | 33% | 50% |
| Co-V-10 | 4.6 | 5.6 | 16% | 52% |
| Co-V-15 | 4.0 | 6.5 | 6% | 53% |

*A cobalt zeolite exchanged with vanadium oxysulfate.

From this data it is apparent that for best yields and selectivity, ratios of Co-V of about 9 or 10 to 4 are desirable. High vanadium ratios give greater selectivity but slower rates.

The weight ratio of metal to support will vary depending upon the number of anionic sites available on the support which can be exchanged. This ratio should be maximized so that all possible anionic sites bear metal. In the case of X-zeolites, for instance, this represents about 15–20% by weight of metal based on the weight of the support.

These aforedescribed catalysts are essentially insoluble in the reaction medium employed in this process. They are, therefore, highly advantageous over the soluble prior art catalysts in that first, they are readily recoverable by filtration, and second, they are stable and may be reused many times without any loss of activity.

The oxidation of the olefins to form the corresponding epoxyalcohols is conveniently carried out in the liquid phase by bubbling air or oxygen into a solution containing the olefin and catalyst for a period of from 1 to 20 hours, depending upon the nature of the olefin starting material, at temperatures of from about 25° to 200° C, and preferably from 50° to 150° C. The oxygen is desirably bubbled through the solution at rates of 0.1 to 100 l./hr. and preferably 1–2 l./hr.

Oxygen pressure may also be used and the rate improves as a result. Pressures up to 1000 psi cause accelerated rates and it is to be expected that higher pressures than this will cause further rate enhancement. Air can also be used in a similar manner but the rate is somewhat slower than with pure oxygen.

The resulting epoxyalcohol is conveniently recovered from the reaction mixture by, for example, vacuum distillation.

The amount of catalyst employed will generally range from about 1 to 10% by weight based on the weight of the olefin. However, it should be understood that this range is not a critical one and may be varied substantially depending upon the activity of the catalyst.

The novel process of this invention will now be illustrated by the following examples.

EXAMPLES

EXAMPLE 1

Formation of Epoxyols from Olefins Using an An X-Zeolite Exchanged with $Cu^{+2}$ and $V^{+4}$ A. Preparation of the Catalyst 100 Grams of an X-zeolite whose acid sites are fully exchanged with sodium (15% Na by weight) is dried at 125° C for 15 hours. A solution of 60.7 grams of $CuCl_2$ in 3300 cc of water is prepared. The sodium-X-zeolite is stirred in contact with 200 mls of the above solution at 40° C for 30 min., filtered and the process repeated 15 times. After 16 copper exchanges the zeolite is washed until it is free of chloride ion and then it is dried at 125° C for 15 hours. Analysis shows the sieve to be over 14% by weight of copper and less than 1% by weight of sodium. The dry copper-exchanged zeolite is labeled XZCu-OV.

The dry copper-exchanged X-zeolite is then exchanged in a similar manner at 40° C, 30 min. with a solution of 36.8 grams of vanadium oxysulfate in 1650 mls of water. The exchange process is summarized below and recovered are four 25 gram batches of catalyst with varying ratios of copper to vanadium. This is accomplished by removing the proper amount of catalyst after 1, 5, 10 and 15 exchanges respectively.

| Exchange No. | Approx. cat. Wt. (gms) Used In Exchange | Total Solution |
|---|---|---|
| 1 | 100 | 300 |
| 2,3,4,5 | 75 | 600(4 × 150) |
| 6,7,8,9,10 | 50 | 500(5 × 100) |
| 11,12,13,14,15 | 25 | 250(5 × 50) |

After exchange 1, ¼ of catalyst is removed (catalyst : XZCu-IV)
After exchange 5, ⅓ of catalyst is removed (catalyst : XZCu-5V)
After exchange 10, ½ of catalyst is removed (catalyst : XZCu-10V)
After exchange 15, remaining catalyst is removed (catalyst : XZCu-15V)

All catalysts are then washed until sulfate-free then dried 15 hours at 125° C.

B. Epoxy-ol Formation Using an X-Zeolite Exchanged with $Cu^{+2}$ snf and $V^{+4}$ 1. Oxidation of Cyclohexene - Cyclohexene (12 ml) and the catalyst (each of those prepared above) (1 g) were charged to a glass reactor at 75° C. Oxygen and bubbled into the solution at a rate of 1.5 l./hr with vigorous stirring over a 5-hour period. The product mixture was analyzed by glpc. Products were separated by vacuum distillation and identified by combination of IR, NMR, and mass spectral data as well as comparison of their g c retention times on columns of several substrates with those of known standards. The results of these reactions are summarized in Table I:

TABLE I

| Catalyst | Conversion,% | Selectivity to Epoxy-ol,% |
|---|---|---|
| XZCu-0V | 41 | 0 |
| XZCu-IV | 21 | 30 |
| XZCu-5V | 20 | 48 |
| XZCu-10V | 12 | 39 |

TABLE I-continued

| Catalyst | Conversion,% | Selectivity to Epoxy-ol,% |
|---|---|---|
| XZCu-15V | 7 | 33 |

Clearly the catalyst giving optimum rate and selectivity was XZCu-5V. The total product analysis for the optimum case was: conversion: 20%, selectivities: 1,2-epoxy-3-hydroxycyclohexane (48%), cyclohexeneoxide (45%),1-cyclohexene-3-ol (3%) 1-cyclohexene-3-one (1%), polymer (41 %).

2. Oxidation of Tetramethylethylene -

Tetramethylethylene (12 ml) and the catalyst (XZCu-5V), (1g) were charged to a 25 ml glass reactor at 50° C. Oxygen was bubbled into the solution at a rate of 1.5 l./min. with vigorous stirring over a 5-hour period. The olefin was converted (24%) to 1,2-epoxy-3-hydroxy-2,3-dimethylbutane in 46% yield. By-products were 2,3-epoxy-2,3-dimethylbutane (40%), 3-hydroxy-2,3-dimethylbutene (9%) and acetone (6%). Products were analyzed, identified, and separated as in 1-B-i above.

EXAMPLE 2

Formation of Epoxyols from Olefins Using an X-Zeolite Exchanged with $Co^{+2}$ and $V^{+4}$ A. Preparation of the Catalyst 100 grams of an X-zeolite which was 15% by weight cobalt and less than 1% by weight sodium was obtained from the sodium form by use of $CoCl_2$ in a procedure similar to that shown in Example 1(A). The dried cobalt-exchanged zeolite was labeled XZCo-OV.

The dried cobalt-exchanged-X-zeolite (50g) was then exchanged 15 times with a solution of 18.4 grams vanadium oxysulfate in 825 mls. water as shown below:

| Exchange | Cat. Wt. | Total Solution |
|---|---|---|
| 1 | 50.0g | 150 ml |
| 2,3,4,5 | 37.5g | 300 ml (4 × 75) |
| 6,7,8,9,10 | 25.0g | 250 ml (5 × 50) |
| 11,12,13,14,15 | 12.5g | 125 ml (5 × 25) |

After 1 exchange removed ¼ cat. (12.5g of XZCo-1V)
After 5 exchanges removed ⅓ cat. (12.5g of XZCo5V)
After 10 exchanges removed ½ cat. (12.5g of XZCo-10V)
After 15 exchanges removed remainder (12.5g of XZCo-15V)

Analyses of Catalysts

| Catalyst | % Co | % V | % Na |
|---|---|---|---|
| XZCo-0V | 15.1 | 0.0 | 3.3 |
| XZCo-1V | 14.8 | 1.1 | 3.0 |
| XZCo-5V | 9.4 | 3.9 | 2.0 |
| XZCo-10V | 4.6 | 5.6 | 0.8 |
| XZCo-15V | 4.0 | 6.5 | 0.5 |

B. Epoxy-ol Formation Using an X-Zeolite Exchanged with $Co^{+2}$ and $V^{+4}$ i. Oxidation of Cyclohexene Oxidations were run under conditions identical to those of Example 1B(i).

| Catalyst | % Co | % V | % Yield After 6 Hrs. | Selectivity to Epoxy-ol |
|---|---|---|---|---|
| Co-V-0 | 15.5 | 0.0 | 30 | 0% |
| Co-V-1 | 14.8 | 1.1 | 36 | 39% |
| Co-V-5 | 9.4 | 3.9 | 33 | 50% |
| Co-V-10 | 4.6 | 5.6 | 16 | 52% |
| Co-V-15 | 4.0 | 6.5 | 6 | 53% |

As noted earlier, it is evident that for best yields and selectivity, ratios of Co-V of about 9 or 10 to 4 are desirable. The total product analysis for the optimum case was: conversion: 33%, selectivities: 1,2-epoxy-hydroxycvclonexane (50%) cyclohexene oxide (39%), 1-cyclohexene-3-ol (2%) 1-cyclohexene-3-one (2%) polymer( 8%).

ii. Oxidation of Tetramethylethylene

Tetramethylethylene (12 ml) and the catalyst, XZCo-5V(1g) were charged to a 25 ml glass reactor at 50° C. Oxygen was bubbled into the solution at a rate of 1.5 l./min with vigorous stirring over a 5-hour period. The olefin was converted (25% to 1,2-epoxy-3-hydroxy-2,3-dimethylbutane in 45% yield. By-products were 2,3-epoxy-2,3-dimethylbutane (40%), 3-hydroxy-2,3-dimethylbutene (10%) and acetone (5%) (analysis by glpc).

iii Oxidation of Indene

Indene (12 mls) is oxidized by a gentle stream of oxygen (1.5 l/min) over a 4 hour period at 75° C using XZCo-5V (1g) as the catalyst. It is converted (11%) to 1,2-epoxy-3-hydroxylhydrinene with a selectivity of 61%.

iv. Oxidation of 3-Phenylpropene 3-phenylpropene (12 mls) in oxidized by a gentle stream of oxygen (1.5 l./min) over a 5 hour period at 100° C using XZCo-5V (1g) as the catalyst. It is converted (46%) to a mixture of 1,2-epoxy-3-hydroxy-3-phenylpropane and 2,3-epoxy-1-hydroxy-3-phenylpropane. The corresponding epoxides and allylic alcohols are minor by-products.

v. Oxidation of 1-Methycyclohexene and 1,2-Dimethylcyclohexene

According to procedures of Example 2-B(i), 1-methyl-cyclohexene and 1,2-dimethylcyclohexene were oxidized to epoxy-alcohols in 58 and 61% yield respectively and 41 and 45% conversion when the catalyst used was XZCo-5V.

EXAMPLE 3

Formation of Epoxyols From Olefins Using an X-Zeolite Exchanged with $Fe^{+2}$ and $V^{+4}$ A. Preparation of the Catalyst An X-Zeolite Exchanged with $Fe^{+2}$ and $V^{+4}$ 100 Grams of an X-zeolite whose acid sites are fully exchanged with sodium (15% Na by weight) is dried at 125° C for 15 hours. A solution of 89.8g $FeCl_2.4H_2O$ in 3300 ml distilled water is prepared. The sodium-X-zeolite is exchanged with 15 200 ml portions of this solution, washed until chloride free, then dried at 125° C for 15 hours. Analysis shows the sieve to be over 14% by weight of iron and less than 10% by weight of sodium.

The dry iron-exchanged-X-zeolite is then exchanged 15 times at 40° C for 30 minutes using a solution of 36.8 grams vanadium oxysulfate in 165 mls of water in a manner identical to example (1) above.

Similarly, four 25 gram samples of Fe-V containing catalysts are obtained.

B. Oxidation of Cyclohexene

When cyclohexene is oxidized in a manner analogous to procedures used in Example 1-B(i), but substituting XZFe-5V as the catalyst, some 1,2-epoxy-3-hydroxycyclohexene is obtained together with other by-products. The catalyst, XZFe-5V, refers to an iron exchanged X-zeolite which has been subjected to five vanadium exchanges as shown in part A of this example.

EXAMPLE 4

Formation of Epoxyols from Olefins Using a Y-Zeolite Exchanged with $Co^{+2}$ nd $V^{+4}$ A. Preparation of the Catalyst 50 grams of a Y-zeolite whose acid sites are fully exchanged with sodium (14% by weight of Na) is dried at 125° C for 15 hours. The sodium ions are exchanged for cobalt ions by the method described above. Back-exchange of the cobalt with vanadium is accomplished in the manner of the previous examples to give four 12.5 gram samples having varying amounts of cobalt and vanadium bound to the Y-zeolite.

| Catalyst | % Co | % V |
|---|---|---|
| YZCo-0V | 14.8 | 0.0 |
| YZCo-1V | 12.6 | 1.0 |
| YZCo-5V | 8.3 | 3.6 |
| YZCo-10V | 4.8 | 5.8 |
| YZCo-15V | 3.9 | 7.3 |

B. Oxidation of Cyclohexene

Using YZCo-5V according to the procedure of Example 1B(i), cyclohexene is oxidized to 1,2-epoxy-3-hydroxy-cyclohexene in high yield.

EXAMPLE 5

Formation of Epoxyols from Olefins Using a Mordenite Exchanged with $Co^{+2}$ and $V^{+4}$ A. Preparation of the Catalyst 50 Grams of ZEOLON-Na, a sodium exchanged synthetic mordenite having the general formula, $Na_2O.Al_2O_3.10SiO_2$, was exchanged with $COCl_2$ in a manner identical to that described in Example (3) to form a cobalt-exchanged pordenite having most the the sodium ions replaced by cobalt. The catalyst at this point is mainly: $CoO.Al_2O_3.10SiO_2$ after drying.

The dry cobalt-exchanged mordenite is then exchanged 15 times at 40° C for 30 minutes with a solution of 1.5 grams vanadium oxysulfate in 5 mls of water in a manner identical to examples (1), (2), and (3) above.

Similarly, four 12.5 gram samples of Co-V exchanged mordenite catalysts are obtained.

B. Oxidation of Cyclohexene

Using MCo-5V according to the procedure of example 1V(i), cyclohexene is oxidized to 1,2-epoxy-3-hydroxy-cyclohexene in 66% yield.

EXAMPLE 6

Formation of Epoxyols from Olefins Using an Amberlyst Resin Exchanged with $Rh^{+3}$ and $V^{+4}$ A. Preparation of the Catalyst Amberlyst-15 beads (a divinylbenzene cross-linked polystyrene matrix having co-polymerized divinylbenzene therein to which are attached nuclear sulfonic acid groups, Rohm and Haas) (50g.) were gently swirled in an excess of an alkaline solution of sodium hydroxide for 24 hours. Gentle swirling was necessary to avoid mechanical grinding and destruction of the beads. Over 90% of the sulfonic acid groups were replaced with sodium ions in this manner.

Sodium-exchanged Amerlyst beads were gently swirled at 50° C in the presence of methanol solutions of rhodium trichloride until most of the sodium was replaced. The rhodium exchanged resin was partially exchanged with methanol solutions of vanadium oxysulfate resulting in catalysts of varying Rh/V ratios.

B. Oxidation of Tetramethylethylene

Using ARh-5V according to the procedures of Example 1B(ii) tetramethyletylene is oxidized to 2,3-epoxy-3-hydroxy-2,3-dimethylbutane in good yield.

The invention claimed is:

1. A catalyst for the oxidation of olefins to form epoxyalcohols comprising a sulfonic acid-type divinylbenzene-polystyrene ion-exchange resin having valence-bonded rhodium and vanadium.

* * * * *